US008940339B2

United States Patent
Wollmer et al.

(10) Patent No.: US 8,940,339 B2
(45) Date of Patent: *Jan. 27, 2015

(54) MICROEMULSIONS AND ITS USE FOR PREVENTING AIRWAY DISEASES

(75) Inventors: Per Wollmer, Akarp (SE); Morgan Andersson, Lund (SE); Lennart Greiff, Lund (SE); Thomas Landh, Lund (SE)

(73) Assignee: Nares AB, Akarp (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,554

(22) Filed: Jun. 12, 2012

(65) Prior Publication Data

US 2013/0115305 A1 May 9, 2013

Related U.S. Application Data

(63) Continuation of application No. 10/563,828, filed as application No. PCT/GB2004/002925 on Jul. 7, 2004, now Pat. No. 8,211,448.

(60) Provisional application No. 60/484,664, filed on Jul. 7, 2003.

(30) Foreign Application Priority Data

Jul. 7, 2003 (SE) ..................................... 0302005
Jul. 7, 2003 (SE) ..................................... 0302006

(51) Int. Cl.
*A61K 9/00* (2006.01)
*A61K 9/107* (2006.01)
*A61K 31/473* (2006.01)
*A61K 31/56* (2006.01)
*A61K 31/573* (2006.01)
*A61K 47/44* (2006.01)

(52) U.S. Cl.
CPC ............. *A61K 9/1075* (2013.01); *A61K 9/0043* (2013.01); *A61K 9/006* (2013.01); *A61K 31/473* (2013.01); *A61K 31/56* (2013.01); *A61K 31/573* (2013.01); *A61K 47/44* (2013.01)
USPC ........................... 424/600; 424/401; 424/403

(58) Field of Classification Search
USPC ......... 424/60, 78.1, 93.1, 178, 234, 400, 401, 424/443, 455, 463; 514/499, 552, 784–786, 514/937, 946, 962
See application file for complete search history.

(56) References Cited

U.S. PATENT DOCUMENTS

| | | | |
|---|---|---|---|
| 5,618,840 A | 4/1997 | Wright | |
| 6,015,832 A | 1/2000 | Hamouda et al. | |
| 6,109,262 A | 8/2000 | Tovey | |
| 6,296,882 B1 | 10/2001 | Viamonte | |
| 8,211,448 B2 * | 7/2012 | Wollmer et al. | 424/400 |
| 2004/0198813 A1 * | 10/2004 | Dennis et al. | 514/499 |

FOREIGN PATENT DOCUMENTS

| | | |
|---|---|---|
| DE | 200 16 125 U1 | 7/2001 |
| DE | 20016125 | 7/2001 |
| EP | 0 242 643 A | 10/1987 |
| EP | 0 242 643 A2 | 10/1987 |
| JP | 7 258070 A | 10/1995 |
| JP | 07258070 | 10/1995 |
| WO | 95/31217 A | 11/1995 |
| WO | WO 95/31217 A | 11/1995 |
| WO | 96/36352 A | 11/1996 |
| WO | WO 96/36352 A | 11/1996 |
| WO | 99/07341 A | 2/1999 |
| WO | WO 99/07341 A | 2/1999 |
| WO | 01/49296 A | 7/2001 |
| WO | WO 01/49296 A | 7/2001 |
| WO | 02/09764 A | 2/2002 |
| WO | WO 02/09764 A | 2/2002 |

OTHER PUBLICATIONS

International Search Report of PCT/GB2004/002925, mailed Nov. 29, 2004.
Patent Abstracts of Japan, vol. 1996, No. 2, Feb. 29, 1996.
Database Internet 'Online!, Nov. 8, 2004, "Automatic translation of JP07-258070 via IPDL".
Bagwe et al., "Improved Drug Delivery Using Microemulsions: Rationale, Recent Progess, and New Horizons", Critical Reviews in Therapeutic Drug Carrier Systems, vol. 18, No. 1, 2001, pp. 77-140, XP001135019.
Inter. Arch. Allergy Immunol. 121: 85-86, 2000.
JAMA, May 19, 1999; 281(19): 1797-1804.
Leser et al, "Self-Assembly of Polar Food Lipids", Advances in Colloid and Interface Science, 123-126 (2006) 125-136.
Sagalowicz et al, "Monoglyceride Self-Assembly Structures as Delivery Vehicles", Trends in Food Science and Technology, vol. 17 (2006), pp. 204-214.
Donovan et al, "Prevention of Murine Influenza A Virus Pneumonitis by Surfactant Nano-Emulsions", Antiviral Chemistry & Chemotherapy 11:41-49, 2000 International Medical Press 095-3202/00/; XP-002304313.

\* cited by examiner

*Primary Examiner* — Michael G Hartley
*Assistant Examiner* — Jagadishwar Samala
(74) *Attorney, Agent, or Firm* — Nixon & Vanderhye P.C.

(57) ABSTRACT

The invention relates to novel microemulsions comprising a non-polar lipid, at least one polar solvent, a surfactant, and a polar lipid. A microemulsion of these ingredients provides an environment that substantially encloses airborne particles, and it can be used for entrapping such particles. The inventive microemulsions are especially adapted for the prevention of symptoms in mammals, which are indirectly or directly caused by airborne particles. The invention further provides compositions comprising such microemulsions and methods of treatment comprising administering the same.

10 Claims, 3 Drawing Sheets

MICROEMULSIONS AND ITS USE FOR PREVENTING AIRWAY DISEASES

This application is a continuation of U.S. application Ser. No. 10/563,828, filed on May 8, 2006, now U.S. Pat. No. 8,211,448, (published as US 2006/0269578 on Nov. 30, 2006), which claims priority to International Application No. PCT/GB2004/002925, filed Jul. 7, 2004; SE Application No. 0302005-4, filed on Jul. 7, 2003, and SE Application No. 0302006-2, filed on Jul. 7, 2003, and claims the benefit of U.S. Provisional No. 60/484,664, filed on Jul. 7, 2003; and the entire contents of each of which is hereby incorporated herein by reference.

The present invention relates to novel microemulsions. More particularly, the invention relates to novel microemulsions, which are useful for the prevention of symptoms in mammals, where such symptoms are indirectly or directly caused by airborne particles.

BACKGROUND OF THE INVENTION

Airway diseases caused by exposure to airborne allergens are major health problems to affluent societies. For example, the prevalence of allergic rhinitis (seasonal, perennial, and occupational) is 20% or more, and increasing. Accordingly, the American Asthma and Allergy Foundation recently reported that about 17 million annual visits to office-based physicians were attributed to allergic rhinitis. Also, they reported that 35 million Americans were allergic to pollen allergens. Besides the morbidity and socioeconomic consequences that these allergies carry themselves, they have been identified as risk factors for the development of asthma. Indeed, one way of preventing the development of bronchial asthma may be to treat the allergic rhinitis condition.

Upper respiratory tract infections (caused by viruses and bacteria) are also major health problems. For example, the common cold is a very prevalent disease: The number of common cold episodes has been estimated to be 5 per year in the 0-4 year old age group, dropping to 3 episodes per year in the 5-19 year old group.

These infections have, notably in the case of the common cold, been identified as a major cause of exacerbations of asthma and "chronic obstructive pulmonary disease".

"Non-allergic, non-infectious (vasomotor) rhinitis" is a less prevalent condition (compared with allergic rhinitis and upper respiratory tract infections). Nevertheless, it is a common differential diagnosis of patients having nasal symptoms.

Pollens and allergens themselves, as well as viruses, bacteria, and other exogenous factors, occur as airborne particles. Pollens typically have diameters between 15-60 μm. Virus particles, on the other hand, are typically 0.1-0.5 μm in diameter, while the size of bacteria and other prokaryotes ranges widely from 0.1 to about 5 μm. Cigarette smoke, printing ink, and occupational factors, which may produce "non-allergic, non-infectious (vasomotor) rhinitis", may also be viewed as particles with a wide size range. In order to produce disease-processes and symptoms associated with allergic rhinitis, upper respiratory tract infections, and "non-allergic, non-infectious (vasomotor) rhinitis" the disease-producing particles must come in contact with the mucosal surface.

Mechanisms leading to allergic rhinitis comprise the contact of inhaled pollens/allergens with the nasal mucosal lining and the interaction with immunocompetent and inflammatory cells residing in the nasal mucosa. Specific antibodies (immunglobulins) are located at the surface of some of these cells. The allergen cross-bridges with receptors on the cell surface, which results in an activation of these cells and in the release of inflammatory mediators. These mediators, in turn, act on certain cells and structures in the mucosa (e.g., glands, blood vessels, nerve endings) to produce inflammation and the symptoms of allergic rhinitis, i.e., nasal itching/sneezing, secretions, and blockage.

Upper respiratory tract infections are caused by viruses and bacteria interacting with the mucosa of the upper airways. The most common cause may be rhinoviruses, which bind to specific mucosal receptors, an inflammatory response being produced. This process, in turn, produces symptoms of common cold (sneezing, watery secretions, reduced nasal patency and catarrhal symptoms with accompanying fever and headache)

"Non-allergic, non-infectious (vasomotor) rhinitis" is sometimes caused by airborne particles other than allergens and infectious agents. The pathophysiological processes give rise to a symptomatology that is very similar to that of allergic rhinitis. However, it is less clearly understood.

The best treatment for type-I allergic diseases, such as allergic rhinitis, would be to avoid the allergen. However, this strategy is more or less impossible, particularly for airborn allergens including those carried by pollens. In addition, this line of reasoning applies for infectious agents and particles causing "non-allergic, non-infectious (vasomotor) rhinitis".

Pharmacological treatments for allergic rhinitis typically aim to mediate the inflammatory pathways outlined above. Commonly use current treatments include topical, oral and systemical gluco-corticosteroids, topical and oral antihistamines, topical chromoglycates, oral leukotriene-antagonists, topical and oral decongestants, topical and oral anticholinergics, and immunotherapy, i.e., repeated exposure to relevant allergens in order to produce a state of increased tolerability. However, there is no single pharmaceutical preparation/treatment available, which treats or reduces all symptoms of allergic rhinitis and such inflammation modulating treatments are not without potential side effects. The most successful treatment may be topical corticosteroids, but their use is associated with a potential risk of local and systemic adverse effects. Antihistaminic preparations are commonly used, but their efficacy is limited. Local decongestants, though used, are not recommended by physicians skilled in the art.

There is currently no established pharmacological treatment for upper respiratory tract infections, except for antibiotics and other chemotherapeutics targeting bacteria, antiviral compounds targeting viruses, specifically influenza virus, as well as topical and oral decongestants.

Antibiotics may be used to treat certain upper respiratory tract infections caused by bacteria. However, no treatment is available for the common cold (caused by viral infections) except for oral and nasal decongestants (alpha-agonists). The neuraminidase inhibitor zanamivir has recently been introduced for the treatment of Influenza A and B, but its efficacy is limited.

Treatments for "non-allergic, non-infectious (vaso-motor) rhinitis" include topical glucocorticosteroids, topical anticholinergics, and topical capsaicin. Common for these treatments, however, is their limited efficacy.

An attempt to overcome nasal mucosal exposure of airborne particles, including pollens, is shown in U.S. Pat. No. 6,109,262, a special adhesive nasal filter being used, which is physically placed within the nasal passages and collects airborne particles. The method and filter disclosed is said to have therapeutic, protective or prophylactic uses.

Inter. Arch. Allergy Immunol. 121:85, 2000, teaches the usefulness of regularly applying a mineral oil to the nasal mucosa of patients with seasonal allergic rhinitis in order to reduce allergic symptoms. It is suggested in this document that fatty acids might be helpful in the prevention of allergic rhinitis. Topical application of fats, such as certain triglycerides and oils to the nasal mucosa, has also been marketed for treating dryness of the nasal mucosa (Nozoil®, Pharmacure Health Care AB, Sweden)

In DE 20016125 a nasal ointment for prophylaxis of inhalation-allergic reactions, especially hay fever, is shown. The ointment comprises a mixture of saturated hydrocarbons and tannin(s), a mechanical barrier film being formed that prevents allergens from entering the nasal mucosa. Likewise, JP 07258070 depicts a nasal rinsing agent for treating allergic rhinitis. The nose cleaning agent, which consists of an oil/water type of emulsion of pH 3.5-5.5, forms an oil film after spraying into a nasal cavity. As in DE 20016125, the oil is spread on the nasal mucosa and a non-homogenous film is formed.

The attachment of most rhinovirus subtypes to cells depends on a cellular receptor, the intercellular adhesion molecule 1 (ICAM-1). JAMA 1999, May 19; 281(19):1797-804, teaches that recombinant soluble ICAM-1, inhaled as a solution or as a powder, reduces the severity of experimental rhinovirus common colds.

Although the above methods attempt to extract airbourne particles prior to reaching the mucosal surfaces, or to form a barrier between the air and the surface, none are believed particularly effective and none are generally indicated as effective against a range of inflammatory conditions. In particular, the films of oil generated are not found to provide effective protection.

Accordingly, there is an obvious need for new and more efficacious treatments also in this topical area. Furthermore, like for allergic rhinits, there is a need for a way of preventing or reducing, in a preventive way, the above-mentioned symptoms associated with upper respiratory tract infections, such as common colds. It would be most desirable if a single composition were effective against a range of such conditions.

It would thus be evidently advantageous to provide a preparation capable of capturing airborne particles, whereby to prevent the above-mentioned problems.

It would be a further advantage to provide preparations that are able to capture airborne particles and retard or inhibit their interactions with exterior mucosal membranes.

It would be still further advantageous to provide preparations that follow the mucus when swallowed or sneezed out (i.e. are eliminated from the body therewith).

These objectives are accomplished by a microemulsion comprising a surfactant, at least one polar solvent, a nonpolar lipid, as well as a polar lipid.

We have now, surprisingly, found that airborne particles, exemplified by virus, bacteria, pollen, allergens, dust, mould, fungus spores, animal dander, and other solid aerosol particles, can be trapped by certain micro-emulsions and thereby their tendency to cause respiratory tract conditions reduced. No similar microemulsion has hitherto been disclosed.

In a first aspect, the present invention thus provides a microemulsion comprising a non-polar lipid, at least one polar solvent, and a surfactant, characterized in that it further comprises a polar lipid.

In a further aspect, the present invention provides a microemulsion suitable for entrapping airborne particles, characterised in that it comprises or consists of a non-polar lipid, at least one polar solvent, a surfactant, a polar lipid and optionally inert carriers and/or excipients, an environment being provided that substantially encloses said particles. In one preferable embodiment, these are the sole ingredients of the microemulsion.

The microemulsions of the present invention are highly useful, both in themselves and in combination with pharmaceutical agents, when formulated as compositions suitable for application to a mammalian subject. In another aspect, the invention thus provides a composition suitable for administration to peripheral membrane linings of, for example, the nose, the eyes, the ears, the pharynx, and/or the larynx of a mammal, characterized in that it comprises a pharmaceutically effective amount of a microemulsion, especially a microemulsion of the invention. Such compositions may, in one embodiment also comprise a drug agent.

In a yet further aspect, the present invention provides a method for preventing airway diseases in a subject, caused directly or indirectly by airbourne particles, said method comprising contacting at least one surface of said subject with a microemulsion or composition of the invention and in a still further aspect the present invention provides a method of preventing airborne particles reaching exterior mucosal membranes of a mammal, said method comprising the step of administering to said exterior mucosal membranes of said mammal a prophylactically effective amount of a microemulsion or composition of the invention.

In a yet still further aspect, the invention provides a microemulsion of the invention for use in therapy and in a still further aspect the invention provides the use of a microemulsion or composition of the invention in the manufacture of a medicament for the treatment or prevention of a disease caused directly or indirectly by airbourne particles, including airway diseases caused by airborne pollen, bacteria and/or viruses.

Without being bound by theory, it is believed that the invention utilizes the inherent properties of an airborne particle. Typically, such a particle can have a hydrophobic core and is at the same time electrostatically charged. Thereby the particle is conferred hydrophilic properties. However, the charge will immediately be lost when entering the nose and contacting a mucous membrane, which results in that the hydrophobic properties will dominate. Thus, when airborne, such particles (pollens etc.) have a hydrophilic surface which must be substantially captured within a hydrophilic environment.

The inventors now believe that oils will not effectively prevent symptoms caused by air-borne particles because such particles are not efficiently wetted by the oils. The oils cannot discharge the surface static charge on the particles and thus cannot wet or encapsulate them.

Similarly, although aqueous systems may discharge the surface of particles, there is then exposed a hydrophobic surface which is not efficiently encapsulated by palor media such as water. It is thus important to note that the nature of the present micro-emulsions is substantially such that they do not "break" to produce an oil film upon application but remain as micro-emulsions.

Microemulsions typically look like clear solutions, but are thermodynamically stable dispersions of one liquid phase into another. The non-polar and polar (e.g. oil and water) domains in the micro-emulsion exhibit a disordered and intricate microstructure. The extremely low interfacial tension of the oil/water interface, the small droplet diameters of approximately 100 nm or less as well as water domains of a suitable size, are advantageous properties for capturing airborne particles.

Average (mode) droplet sizes (diameters) in the microemulsions of the invention will generally be 5 to 200 nm, particularly 10 to 150 nm and more preferably 20 to 100 nm. It is preferable, in order to preserve the micro-emulsion nature of the composition, that no detectable proportion of droplets (for example less than 0.1%) exceed 500 nm, preferably no more than this will exceed 350 nm and most preferably no more than 0.1% will exceed 250 nm. Droplet sizes may be measured by techniques well known to those of skill in the art. In particular, laser light scattering/diffraction methods are standard. Methods involving techniques such as Rayleigh Scattering or cryo-TEM may, however, be necessary to examine particle sizes below around 300 nm.

It is the inventor's non-binding theory that airborne particles can be trapped by the specific self-assembled hydrophilic/hydrophobic structure provided by means of the invention. The micro-emulsions of the invention are able to provide an environment, which substantially encloses (surrounds) the particles.

In addition, the inventive microemulsion need not contain any active agent, such as a drug or the like. In this embodiment, no side-effects originating from such agents are thus obtained.

Furthermore, a sprayable microemulsion can be provided, which contains large amounts of a polar solvent in order to reduce the viscosity. In addition, the microemulsions of the invention are able to top spread homogenously on the mucosa and do not only function as a protective barrier but also as a capturing agent for airborne particles, which follows the mucus when swallowed or sneezed out. In this way particles are efficiently captured, prevented from interaction with the mucosal surfaces and then removed from the area of interaction.

The microemulsions according to the invention are effective for the protection of mucosal membranes that line all body cavities which are open to the exterior. Thus, peripheral membrane linings of the nose, the eyes, the ears, the pharynx, and the larynx can be protected. However, it is preferred to be used for capturing particles in the nasal cavity, the pharynx, and/or the larynx.

A microemulsion can be defined as a thermodynamically stable, transparent dispersion of two immiscible liquids, stabilized by an interfacial film of surfactants. In this connection a microemulsion is a clear thermodynamically stable dispersion of two immiscible liquids containing appropriate amounts of surfactants and co-surfactants.

A microemulsion generally comprises at least one continuous phase and a further phase which typically comprises discontinuous, dispersed "droplets". It will be clear to one of skill in the art that, depending upon the type and proportion of lipids chosen for a particular emulsion, these droplets may be disordered, "liquid" droplets, and/or may have a regular or irregular internal structure, such as that of a cubic or hexagonal liquid crystalline, lamellar, or "sponge" phase. All of such droplets will evidently be included in the scope of the microemulsions described herein. In one preferred embodiment, the droplets comprise liquid phase non-polar lipid.

The meaning of surfactant as used in the description and in the claims follows the current usage well known to those skilled in the art. A good surfactant should have a low solubility in both the bulk and dispersed phases of the microemalsion.

The surfactant is usually an organic polymer with a long chain hydrophobic tail and a small hydrophilic head group, and it can be anionic, nonionic, cationic or ampheoteric. Nonionic surfactants are preferred since they are less harmful to humans than ionic surfactants.

Suitable nonionic surfactants are polyoxyethylenated alkylphenols (mostly p-octyl-, p-nonyl-, p-dodecyl-, di-nonylphenols), polyoxyethylenated straight chain alcohols, polyoxyethylenated polyoxypropylene glycols, polyoxyethylenated mercaptans, long chain carboxylic acid esters (glyceryl and polyglyceryl esters of natural fatty acids, propylene glycol, sorbitol, and polyoxyethylenated sorbitol esters, polyoxyethylene glycol esters) and alkanolamines (diethanolamine-, isopropanolamine-fatty acid condensates) The edible surfactants are mainly the esters based on glycerol, sorbitol, and propylene glycol.

Preferably, the surfactant is an amphiphilic compound such as a polysorbate, a poloxamer, or a fatty acid poly-oxyethylene. It is most preferred that the amphiphilic compound is polysorbate 80.

Suitable ionic surfactants are succinic, citric, and diacetyl tartaric acid esters. Lecithin is the preferred surfactant containing a positive charge.

The required amount of surfactant is dependent on the other components used in the inventive microemulsion. However, the surfactant concentration should always exceed its critical micellar concentration (CMC).

The hydrophilic/hydrophobic balance, i.e. the molar ratio of hydrophilic to hydrophobic moieties, has a temperature maximum in the mutual solubility of the surfactant in water and oil. This maximum is adapted to encompass a temperature interval, within which the inventive microemulsion is intended to be used, for example around room and body temperatures. Preferably, the hydrophilic-hydrophobic balance of the surfactant, should not exceed 7. Thus, the surfactant comprises 0.1 to 20% (wt/wt), preferably 1 to 10% (wt/wt) of the microemulsion.

The surface tension between the two liquid layers of the microemulsion can be further lowered to approach zero by the addition of at least one polar solvent. Thus, the polar solvent may act as a cosurfactant in the inventive microemulsion and is preferably a small molecule that improves the stability of the microemulsion system. Increased amounts of polar solvent also reduces the viscosity, a better micro-viscosity being obtained in the microemulsion droplets.

Typically, such polar solvents are short chain alcohols, e.g. ethanol to butanol, glycols, such as propylene glycol, or medium chain alcohols, amines, or acids. Preferred polar solvents are propylene glycols and/or polyethylene glycols and/or a saline solution.

Water and buffered aqueous media can also be used for solubilizing one phase into the other in the microemulsion system, which contain a variety of salts and buffers. Preferably, the salts are alkali and alkaline earth halides, e.g. sodium chloride, potassium chloride, or sodium sulphate. Various buffers may be used, such as citrate, phosphate, HEPES, Tris, or the like to the extent that such buffers are physiologically acceptable for its purpose.

Evidently, the polar solvent may be included in the microemulsion at the time of application, and this forms a preferred aspect of the invention. In an alternative aspect, however, the polar liquid may be incorporated into the microemulsion at the point of application, either during application (e.g. by co-application of a lipid/surfactant mixture and a solvent) or by adsorption of liquid (especially aqueous liquid) from the mucosal surface upon contact therewith. In this aspect, the "microemulsion" may be seen, in fact, as a "microemulsion precursor" but it will be evident that in both cases the result and functioning of the invention will be equivalent and thus both aspects are encompassed in the present description, where context allows. It will be necessary, however that where a "microemulsion precursor" is used, this will generate a true microemulsion as indicated herein, to at least a sufficient extent to provide the advantageous effects indicated.

The polar solvent or solvents, where present in the inventive microemulsion should comprise 5 to 95% (wt/wt), preferably 10 to 55% (wt/wt) of the same. It is also preferred that the at least one polar solvent has a pH exceeding pH 5.5.

The polar lipid in the microemulsion can be a suitable amphiphilic alcohol or amine, a sterol (e.g. cholesterol), a fat soluble vitamin, a glyceride, a phospholipid, a glycolipid, a sphingolipid, or any mixture thereof. Preferably, where present the glyceride is a mono-acyl glyceride, for example glyceryl monooleate, glyceryl monolinoleate or glyceryl monolinenoleate.

The polar lipid may comprise 1 to 99% (wt/wt), preferably 10 to 75% (wt/wt), most preferred 20 to 50% (wt/wt) of the microemulsion of the invention.

It is an important aspect of the invention that the microemulsion in itself, consisting of a non-polar lipid, at least one polar solvent, a surfactant, and a polar lipid as sole ingredients (optionally with inert carrier or excipients), provides an environment that can both wet and substantially enclose airborne particles.

The microemulsion of the invention should also comprise one or more non-polar lipids, such as di-acyl glycerides, triacyl glycerides, mineral oils, paraffin oils and esters, as well as ethers or waxes of fatty acids having a total number of carbon atoms more than 22. Preferably, the nonpolar lipid is a tri-acyl glyceride.

Excellent microemulsions are formed well by using non-polar oils, such as the normal alkanes, as the nonpolar lipid. Triglycerides are preferred because they are edible but other lipids may be used individually or as mixtures in any amount which can be adequately tollerated.

Evidently, components such as triglycerides may be made or modified synthetically or extensively purified. Alternatively and preferably, these may be used as available mixtures, such as those from natural sources. Natural sources include animal oils and plant/vegetable oils.

Acceptable animal oils include cod liver oil, lanolin oil, mink oil, orange roughy oil, and shark liver oil. Acceptable vegetable oils include almond, apricot kernel, avocado, castor, coconut, corn, evening primrose, jojoba, olive, safflower, sesame, soybean, and wheat germ oils. Some silicone oils are acceptable, such as certain linear polysiloxanes and cyclic dimethyl polysiloxanes such as cyclomethicone. It is preferred that the vegetable oil is sesame oil.

The non-polar lipid should comprise 1 to 99% (wt/wt), preferably 5 to 75% (wt/wt), most preferably 5 to 35% (wt/wt) of the microemulsion.

The microemulsion according to the invention can have a large number of applications where airborne particles have to be entrapped in the homogenous (microemulsion) film formed. These include different kinds of filter devices, which can be used for e.g. air cleaning and/or decontamination. However, the inventive emulsion is especially adapted for direct human use, i.e. to be applied to peripheral membrane linings of the nose, the eyes, the ears, the pharynx, and the larynx for entrapping airborne particles.

The microemulsions can be applied locally. Local applications include for example spray and drops, pipettes made up in single doses, a powder obtained by lyophilization of the emulsion, a tamponage, or a painting. A nasal pool device can be used no apply controlled amounts of the emulsion on a human nasal airway mucosa. Preferably, a mouth or nasal spray device is used, which contains the inventive microemulsion.

Where a powder is used, this may be conveniently generated by drying the microemulsions of the invention, which will thus form solvent-free or low-solvent microemulsion precursors. These precursors will again form (to at least some extent) the true microemulsions upon contact with, and incorporation of, aqueous fluids at the mucosal surface. Obviously, a convenient method for generating a dry powder microemulsion/precursor will be freeze-drying but the skilled worker will be aware of many equivalent techniques such as spray-drying which may be used to generate dry powders. Powders may also be milled and/or agglomerated to control particle sizes.

Where a powder is generated, it may also be advantageous to include other agents to improve the drying, the handling properties of the powder and/or the resuspension of the lipid components into a regenerated microemulsion. Suitable agents are generally water soluble and include polymers, salts and sugars.

The present invention focuses on, but is not limited to, those initial stages of the inflammatory process which take place at or in the peripheral membrane linings of the nose, the eyes, the ears, the pharynx, and the larynx. For example, at or in the nasal mucosa, an inflammation may result in increased levels of pro-inflammatory chemokines and cytokines, recruitment and activation of specific inflammatory cells, and changes in end-organ functions of the mucosa (e.g., the microcirculation, the secretory apparatus and the ciliary system). Inflammatory processes, although in part characterized by different inflammatory cells, are also associated with upper respiratory tract infections. In one aspect of the presention, there is thus provided a composition comprising a microemulsion of the invention plus an active agent. In particular, this active agent will generally be a pharmaceutical agent having a local effect upon these inflammatory cells, systems or symptoms. In a preferred embodiment the present invention thus provides a composition comprising a microemulsion of the invention and a locally acting drug.

Suitable locally acting drugs include anti-allergical drugs, such as glucocorticosteroids, antihistamines, leukotriene antagonists, chromoglycates, decongestants, such as alpha-agonists, anti-cholinergic drugs, and anti-infection drugs, such as antibiotics or anti-viral compounds. Particularly suitable drugs include budesonide, beclomethasone dipropionate and loratadine. Mixtures of such drugs are also suitable. Compositions of the present invention may require no additional carriers but, where desirable, any suitable pharmaceutically tollerable carrier or excipient may be included.

EXAMPLES

The invention will now be further described and illustrated by reference to the following examples. It should be noted, however, that these examples should not be construed as limiting the invention in any way. The disclosure of all references cited in all sections of this text are incorporated herein by reference.

Example 1

Preparation of an Exemplary Composition

Twenty ml of a microemulsion was prepared, which had the following composition (w/w %)

| Component | Amount (w/w %) |
|---|---|
| Glycerol monooleate | 34 |
| Propylene glycol | 23 |
| Polyethylene glycol 400 | 18 |

-continued

| Component | Amount (w/w %) |
|---|---|
| Sesame oil | 11 |
| Saline solution | 10 |
| Polysorbate 80 | 4 |

Example 2

Adverse Effects

The microemulsion according to Example 1 was filled on flasks equipped with a spray mechanism an administered to human volunteers. No signs or complaints of adverse effects were made.

Example 3

Wetting Behaviour and Spreading Over Surfaces

The wetting behaviour of a formulation was studied and compared to wetting by aqueous and oil reference solutions (compositions as given in Table 1). The model surfaces were glass microscope slides treated either by washing with ethanol or by heating to 450° C. overnight to obtain clean surfaces.

The evolution of liquid lenses were followed visually after applying 20 µL or 50 µL on top of the clean horizontally positioned glass surfaces. After 15 minutes the diameters of the liquid lenses were measured (Table 2). It can be seen that formulation 1 has a superior wetting of both surfaces as compared with sesame oil and pure saline.

TABLE 1

Compositions

| | GMO (wt %) | PG (wt %) | PEG 400 (wt %) | Sesame oil (wt %) | Saline (wt %) | P80 (wt %) |
|---|---|---|---|---|---|---|
| Form. 1 | 35.9 | 24.3 | 19.0 | 11.6 | 5.0 | 4.2 |
| Ref. 1 | | | | | 100 | |
| Ref. 2 | | | | 100 | | |

TABLE 2

Diameter of the liquid lenss after 15 minutes

| | EtOH treated glass surface Diameter of liquid lens (mm) | | Heat treated glass surface Diameter of liquid lens (mm) | |
|---|---|---|---|---|
| | 20 µL drop | 50 µL drop | 20 µL drop | 50 µL drop |
| Form. 1 | 9 | 14 | 12.5 | 18 |
| Ref. 1 | 7 | 9.5 | 12.5 | 15.5 |
| Ref. 2 | 8 | 12 | 7 | 11 |

Example 4

Engulfment of Timothy Pollen

Timothy pollen grans, Phleum pratense (Allergon, batch 011303101) where contacted with formulation 1, reference 1, or reference 2 (see Example 3). The process was performed on microscope slides (ethanol washed) and followed in the light microscope. Saline (ref. 1) wetted the pollen grains and the entities were quickly engulfed. A similar situation was found with formulation 1, while with reference 2 (sesame oil) this process was much slower and engulfment did not readily take place.

Example 5

Prevention of Pollen Allergy

In order to test the feasibility of a nasal provocation the microemulsion according to Example 1 was administered to the nasal cavity of 9 subjects by means of a nasal pool device (Greiff L et al. Clin Exp Allergy 1990 May; 20(3):253-9). Also the placebo (saline solution) was administered with this device.

Rinsing was performed by loading and administrating 14 ml of saline solution with this nasal pool device.

Nasal provocations were performed at two occasions with at least one week in between. The study was of a single blind placebo controlled fashion. At one visit the microemulsion of Example 1 was given and at the other occasion the placebo (isotonic saline). Both treatments (microemulsion and placebo) were given in the nasal pool device (14 ml) in the right nasal cavity.

Before the challenge nasal symptoms were rated, followed by two nasal washings (each, one minute) using the pool device. These washings with 14 ml of saline were undertaken in order to reduce cell free mediators that have been accumulated on the nasal mucosal surface. Thereafter a 5 min saline washing was performed in order to establish a baseline.

The microemulsion and placebo (saline) were delivered by means of the pool device in a randomized order. The treatments (placebo and saline) were being kept in contact with the nasal mucosal surface for 2.5 minutes.

Then the treatment was released and the subjects assessed symptoms once more. Five min after the treatment delivery a nasal allergen challenge with a moderate dose of allergen was given in the same nasal cavity in the same way as the previous washings and treatments had been delivered (right nasal cavity). The subjects performed 10 min after allergen challenge a third symptom assessment and a second 5 min washing was performed as well. Both 5 min washings were collected and immediately cold centrifuged at 2000 rpm and frozen ($-18°$ C.) for later analysis.

Nasal symptoms were scored, as previously described, prior to challenge (baseline), immediately before challenge (prior) and 10 mm after allergen challenge. Nasal symptoms, runny nose, and blockage were scored 0=no symptoms, 1=mild symptoms, 2=moderate symptoms, 3=severe symptoms. In addition, the number of sneezes were counted.

Sneezing

The number of sneezes were determined at baseline, prior to and 10 min after allergen challenge in 9 subjects with pollen allergy after pretreatment with the microemulsion and placebo.

Allergen induces sneezes in the allergic subjects both after microemulsion and placebo treatment with no significant differences between the treatments.

Rhinitis

A subjective assessment of nasal secretion was also performed at baseline, prior to and 10 min after allergen challenge, in 9 subjects with pollen allergy after pretreatment with the microemulsion and placebo.

Allergen induces nasal secretion in the allergic subjects both after treatment with microemulsion and placebo with no significant differences between the treatments.

Nasal Congestion

Likewise, a subjective assessment of nasal congestion was performed at baseline, prior to and 10 min after allergen challenge, in 9 subjects with pollen allergy after pretreatment with the microemulsion and placebo.

Allergen challenge increases nasal congestion in the allergic subjects both after treatment with microemulsion and placebo. However, the microemulsion significantly reduces nasal congestion as compared to placebo (*=p<0.05).
Total Nasal Symptom Score.

FIG. 1 shows the assessment of total nasal symptom score with reference to sneezing, secretion, and nasal congestion.

Allergen challenge increases the total nasal symptom score in the allergic subjects both after treatment with microemulsion and placebo. However, the microemulsion significantly reduces total symptoms as compared to placebo (*=p<0.011).

TABLE 4

Total nasal symptom score measured at baseline, after treatment and after challenge. Values are means ± s.e.m.

|  | Microemulsion | Placebo |
|---|---|---|
| Baseline | 0.9 ± 0.3 | 1.0 ± 0.2 |
| After treatment | 1.4 ± 0.4 | 1.0 ± 0.3 |
| After challenge | 4.4 ± 0.6 | 6.1 ± 0.5 |

Example 6

Nasal Mucosal Inflammation

α2-Macroglobulin was measured in nasal washings as an index of nasal mucosal inflammation. Samples were collected prior to and 10 min after allergen challenge in 9 subjects with pollen allergy after treatment with the microemulsion according to Example 1 and placebo.

As shown in FIG. 2, the allergen challenge induces a significant increase in nasal mucosal output of α2-macroglobulin after placebo treatment (*=p<0.01), but not after treatment with the microemulsion. Furthermore, a significant difference in the levels of α2-macroglobulin is seen between microemulsion and placebo 10 min after allergen challenge (*p<0.05).

TABLE 5

Mucosal output of $\alpha_2$-macroglobulin at baseline and after provocation. Values are means ± s.e.m. and units are μg/ml.

|  | Microemulsion | Placebo |
|---|---|---|
| Baseline | 0.36 ± 0.16 | 0.26 ± 0.07 |
| After challenge | 1.5 ± 0.9 | 3.1 ± 1.9 |

Example 7

Viscosity Control in Formulations

The viscosity of the formulation can be controlled and reduced by suitable compositional variations. The compositions and viscosities for 4 formulations is shown in Table 6 and FIG. 3.

TABLE 6

Compositons of various formulations and their Newtonian viscosities at 25° C.

|  | GMO (wt %) | PG (wt %) | PEG 400 (wt %) | Sesame oil (wt %) | Saline (wt %) | P80 (wt %) | GML (wt %) | AkoMed (wt %) | Viscosity (mPas) |
|---|---|---|---|---|---|---|---|---|---|
| Form. 1 | 35.9 | 24.3 | 19.0 | 11.6 | 5.0 | 4.2 |  |  | 109 |
| Form. 2 | 37.8 | 25.6 | 20.0 | 12.2 |  | 4.4 |  |  | 99 |
| Form. 3 |  | 24.3 | 19.0 |  | 5.0 | 4.2 | 35.9 | 11.6 | 73 |
| Form. 4 |  | 25.6 | 20.0 |  |  | 4.4 | 37.8 | 12.2 | 64 |

Example 8

Formulations with Active Components

The following composition was prepared, as described in Example 1.

| Component: | Amount (w/w %) |
|---|---|
| Glycerole monooleate | 34 |
| Propylene glycol | 23 |
| Polyethylene glycol 400 | 18 |
| Sesame oil | 11 |
| Saline | 10 |
| Polysorbate 80 | 4 |

Formulations containing active component were then prepared by adding 2.5 mg of the active component to 5 mL of the composition. The formulations were gently warmed to 39° C. to facilitate dissolution. The final concentration of the active component was thus approximately 0.5 mg/ml, which corresponds to the concentration used in commercially available formulations of these substances.

The following active components were used: budesonide, beclomethasone dipropionate and loratadine.

Example 9

Clinical Study No. 2

A clinical study with another composition was performed in nine allergic patients. The design was as for Example 5. The study was cross-over with saline as control. Symptom scores were obtained at baseline, after treatment (saline or microemulsion) and after pollen challenge. Nasal mucosal inflammation was, however, not measured in this study.

| Comonent: | Amount (w/w %) |
|---|---|
| Glycerole monooleate | 37.8 |
| Propylene glycol | 25.6 |
| Polyethylene glycol 400 | 20.0 |
| Sesame oil | 12.2 |
| Polysorbate 80 | 4.4 |

TABLE 7

Total symptom scores (mean ± s.e.m.) obtained in Clinical study No. 2

|  | Placebo | Microemulsion |
|---|---|---|
| Baseline | 0.4 ± 0.2 | 0.3 ± 0.2 |
| After treatment | 0.5 ± 0.3 | 1.2 ± 0.3 |
| After challenge | 4.6 ± 0.3 | 3.7 ± 0.7 |

The study shows that the symptom score is lower when allergen provocation is performed after treatment with the microemulsion than after treatment with placebo.

Example 10

Protection Against Viral Infection

The ability of the microemulsions to protect against viral infection was studied in cell cultures. Cell monolayers from two different cell lines were grown in well plates. The cell lines used were Madin-Darby canine kidney cells (MDCK) and human salivary gland cells (HSG). Human Influenza A virus was used in the experiments. The amount of virus used was 15 times the amount required to infect 50% of the cells in a well.

Two exemplary compositions were examined. These were prepared as illustrated in Example 1.

|  | Amount (w/w %) | |
|---|---|---|
| Component: | Example A | Example B |
| Glycerole monooleate | 35.9 | 37.8 |
| Propylene glycol | 24.3 | 25.6 |
| Polyethylene glycol 400 | 19.0 | 20.0 |
| Sesame oil | 11.6 | 12.2 |
| Saline | 5.0 | 0 |
| Polysorbate 80 | 4.2 | 4.4 |

Experiment 1—Premixing Virus with Composition

Virus was mixed with 5 or 10 μL of the compositions A or B and then added onto the cell culture. The well plates were incubated for one hour at 37° C. The compositions were then washed off and the plates incubated for further 24-48 hours. The cells were then fixed and the degree of infection was measured by solid-phase ELISA (enzyme linked immunosorbent assay). The degree of infection was measured by spectrophotometry as absorbance at 490 nm. The result is expressed as optical density at 490 nm. Virus without addition of the composition was used as control.

TABLE 8

Results obtained with Example A in the two different cell lines. Results are presented as mean value ± SD

|  | Optical density at 490 nm | | |
|---|---|---|---|
| Cell line | 0 μL (control) | 5 μL | 10 μL |
| MDCK | 3341 ± 150 | 1690 ± 1316 | 1154 ± 1240 |
| HSG | 659 ± 162 | 390 ± 116 | 293 ± 75 |

TABLE 9

Results obtained with Example B in the two different cell lines. Results are presented as mean value ± SD

|  | Optical density at 490 nm | | |
|---|---|---|---|
| Cell line | 0 μL (control) | 5 μL | 10 μL |
| MDCK | 3191 ± 213 | 1988 ± 1331 | 1629 ± 1318 |
| HSG | 837 ± 68 | 569 ± 119 | 437 ± 71 |

Experiment 2—Cells Pretreated with Composition

Compositions A or B were added to cell cultures in a well plate. The amount of compositions used were 5, 10, 15 and 20 μL. Virus was then added to the well. The well plates were incubated for one hour at 37° C. The compositions were then washed off and the plates incubated for further 24-48 hours. The cells were then fixed and the degree of infection was measured by solid-phase ELISA (enzyme linked immunosorbent assay). The degree of infection was measured by spectrophotometry as absorbance at 490 nm. The result is expressed as optical density at 490 nm. Virus without addition of the composition was used as control.

TABLE 10

Results obtained with Example A in the two different cell lines. Results are presented as mean value ± SD

|  | Optical density at 490 nm | | | | |
|---|---|---|---|---|---|
| Cell line | 0 μL (control) | 5 μL | 10 μL | 15 μL | 20 μL |
| MDCK | 1981 ± 569 | 1004 ± 1347 | 312 ± 1226 | −210 ± 219 | −312 ± 61 |
| HSG | 250 ± 211 | −49 ± 75 | −85 ± 204 | −181 ± 46 | −203 ± 67 |

TABLE 11

|  | Optical density at 490 nm | | | | |
|---|---|---|---|---|---|
| Cell line | 0 μL (control) | 5 μL | 10 μL | 15 μL | 20 μL |
| MDCK | 2319 ± 109 | 418 ± 1143 | 1396 ± 1476 | 172 ± 31 | −150 ± 67 |
| HSG | 445 ± 368 | −1 ± 184 | −94 ± 105 | −148 ± 96 | −156 ± 231 |

The results show that both Example A and Example B protects the cells in the culture from infection with Influenza A virus.

Figure 1:
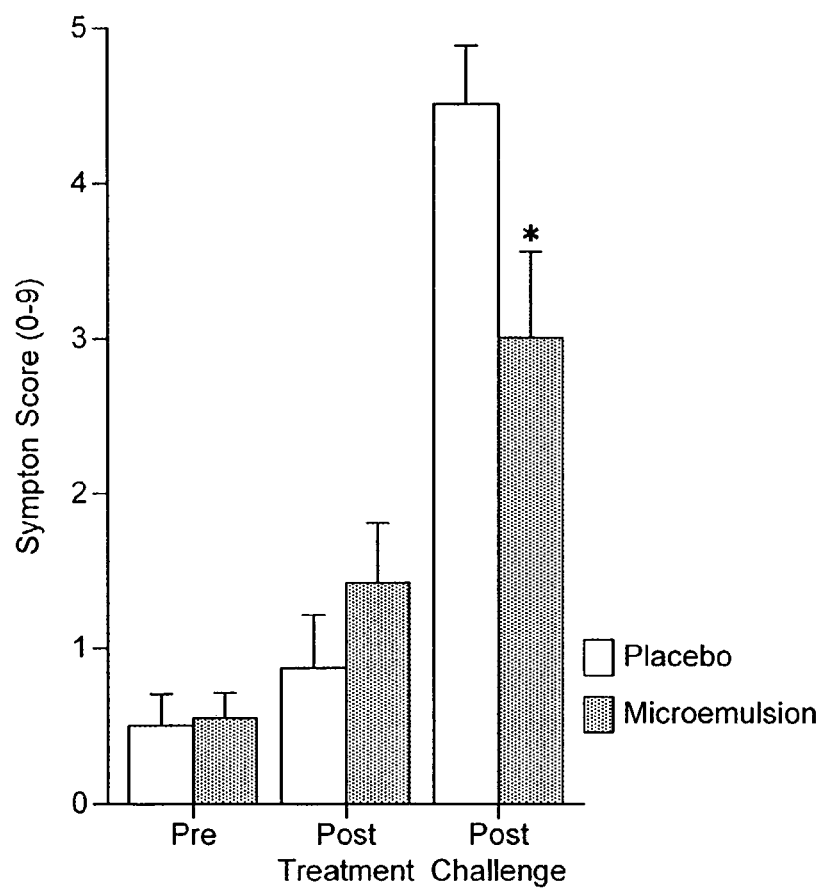
FIG. 1 shows the assessment of total nasal symptom score with reference to sneezing, secretion, and nasal congestion.
Figure 2:
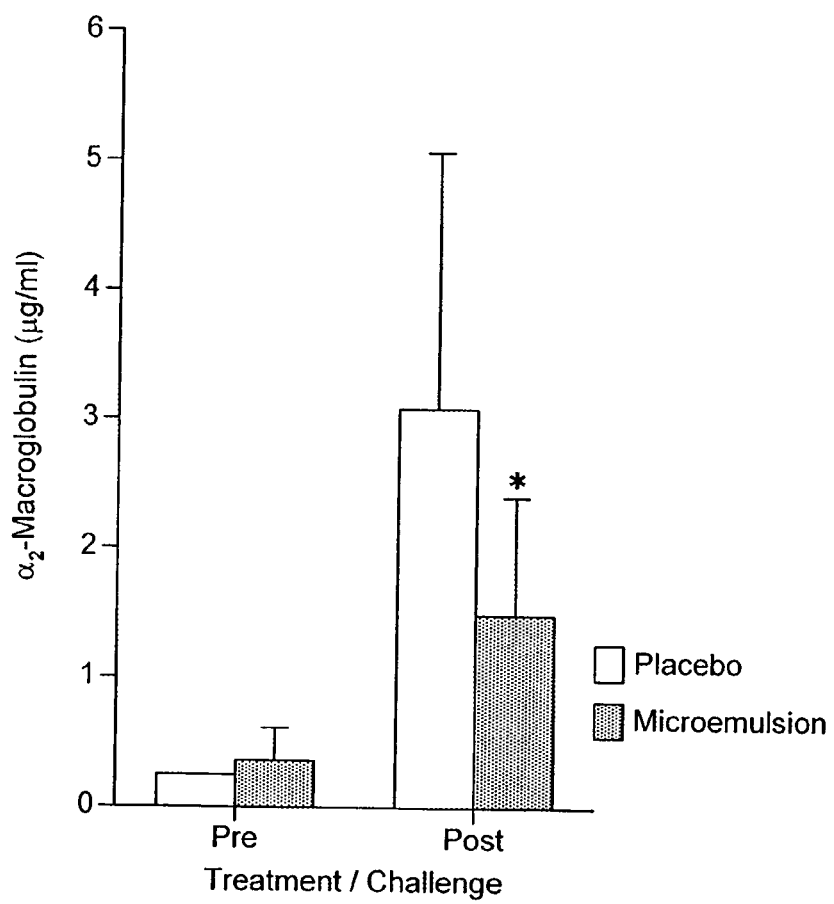
FIG. 2 shows that the allergen challenge induces a significant increase in nasal mucosal output of .alpha. 2-macroglobulin after placebo treatment (*=p<0.01), but not after treatment with the microemulsion.
Figure 3:
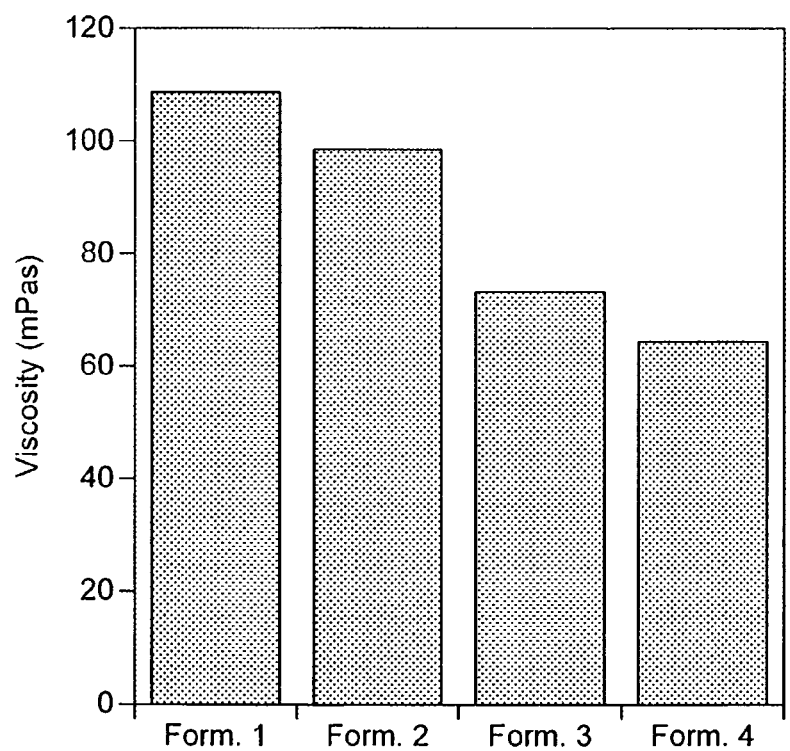
FIG. 3 shows the viscosities for 4 formulations.

The invention claimed is:

1. A composition suitable for administration to peripheral membrane linings of the nose, the eyes, the ears, the pharynx and/or the larynx of a mammal characterized in that said composition comprises a pharmaceutically effective amount of a microemulsion comprising 5 to 35 wt % of a non-polar animal or vegetable oil, 10 to 55 wt % of at least one polar solvent selected from the group consisting of water, a buffer, an alcohol, and mixtures thereof, and at least one surfactant selected from a polysorbate, a poloxamer and a fatty acid polyoxyethylene, wherein the microemulsion further comprises 20-50 wt % of a monoacyl glycerol;
wherein said composition also comprises a pharmaceutical active agent.

2. The composition as claimed in claim 1 wherein said pharmaceutical active agent is a locally acting drug.

3. The composition as claimed in claim 1 wherein said pharmaceutical active agent is an anti-allergical drug, a decongestant, or an anti-infection drug.

4. The composition as claimed in claim 1 wherein said pharmaceutical active agent is budesonide, beclomethasone dipropionate and loratidine.

5. The composition as claimed in claim 1 wherein said microemulsion is suitable for entrapping airbourne particles and consists of 5 to 35 wt % of a non-polar animal or vegetable oil, 10 to 55 wt % of at least one polar solvent selected from the group consisting of water, a buffer, an alcohol, and mixtures thereof, and at least one surfactant selected from a polysorbate, a poloxamer and a fatty acid polyoxyethylene, wherein the microemulsion further comprises 20-50 wt % of a monoacyl glycerol.

6. A method of entrapping airborne particles in order to reduce their tendency to directly or indirectly cause respiratory tract conditions in a subject, said method comprising contacting at least one surface (preferably at least one mucosal surface) of said subject with a composition comprising 5 to 35 wt % of a non-polar animal or vegetable oil, 10 to 55 wt % of at least one polar solvent selected from the group consisting of water, a buffer, an alcohol, and mixtures thereof, and at least one surfactant selected from a polysorbate, a poloxamer and a fatty acid polyoxyethylene, wherein the microemulsion further comprises 20-50 wt % of a monoacyl glycerol;
wherein said composition optionally also comprises a pharmaceutical active agent.

7. A method of retarding or inhibiting the interaction of airborne particles with the mucosal membranes of a mammal, said method comprising the step of administering to said exterior mucosal membranes of said mammal a prophylactically effective amount of a composition suitable for administration to peripheral membrane linings of the nose, the eyes, the ears, the pharynx, and/or the larynx of a mammal, characterized in that said composition comprises a pharmaceutically effective amount of a microemulsion comprising 5 to 35 wt % of a non-polar animal or vegetable oil, 10 to 55 wt % of at least one polar solvent selected from the group consisting of water, a buffer, an alcohol, and mixtures thereof, and at least one surfactant selected from a polysorbate, a poloxamer and a fatty acid polyoxyethylene, wherein the microemulsion further comprises 20-50 wt % of a monoacyl glycerol;
wherein said composition optionally also comprises a pharmaceutical active agent.

8. The method as claimed in claim 7, wherein said composition is administered buccally or intranasally.

9. A method of entrapping airborne particles in order to reduce their tendency to directly or indirectly cause respiratory tract conditions in a subject, including airway diseases caused by airbourne pollen, bacteria and/or viruses, said method comprising contacting at least one surface of said subject with a composition comprising 5 to 35 wt % of a non-polar animal or vegetable oil, 10 to 55 wt % of at least one polar solvent selected from the group consisting of water, a buffer, an alcohol, and mixtures thereof, and at least one surfactant selected from a polysorbate, a poloxamer and a fatty acid polyoxyethylene, wherein the microemulsion further comprises 20-50 wt % of a monoacyl glycerol.

10. The method as claimed in claim 9 wherein said disease is allergic rhinitis, the common cold, upper respiratory tract infection caused by viruses, upper respiratory tract infection caused by bacteria and/or non-allergic, non-infectious rhinitis.

* * * * *